(12) United States Patent
Berg et al.

(10) Patent No.: US 7,538,334 B2
(45) Date of Patent: May 26, 2009

(54) DEVICES AND METHODS FOR TARGETING PRINTING PLATES AND MEASURING DOT COVERAGE THEREON

(75) Inventors: Bernard J. Berg, Wayland, MI (US); Peter G. Vander Jagt, Belmont, MI (US); Rob Kuschinsky, Hudsonville, MI (US); Chris Lafontaine, Ada, MI (US); Jon K. Nisper, Grand Rapids, MI (US); Michael J. Weber, Rockford, MI (US)

(73) Assignee: X-Rite, Inc., Grand Rapids, MI (US)

( * ) Notice: Subject to any disclaimer, the term of this patent is extended or adjusted under 35 U.S.C. 154(b) by 216 days.

(21) Appl. No.: 11/517,911

(22) Filed: Sep. 8, 2006

(65) Prior Publication Data
US 2007/0051880 A1    Mar. 8, 2007

Related U.S. Application Data

(60) Provisional application No. 60/788,899, filed on Apr. 3, 2006, provisional application No. 60/715,117, filed on Sep. 8, 2005.

(51) Int. Cl.
G01N 21/86    (2006.01)
G01V 8/00    (2006.01)

(52) U.S. Cl. ............... 250/559.07; 250/559.08; 250/208.1; 356/237.2; 356/364

(58) Field of Classification Search ............ 250/559.04, 250/559.25, 559.07, 559.08, 559.48, 559.29, 250/559.23, 208.1; 356/237.2, 364, 71, 72
See application file for complete search history.

(56) References Cited

U.S. PATENT DOCUMENTS 4,262,208 A * 4/1981 Suzki et al. ............ 250/548
5,185,644 A * 2/1993 Shimoyama et al. ........ 356/369
2003/0049039 A1* 3/2003 Suzuki ..................... 399/49
2003/0143488 A1* 7/2003 Teng ........................ 430/303
2004/0179922 A1* 9/2004 Blake et al. ................ 414/411
2005/0073596 A1* 4/2005 Takahashi ................. 348/241

FOREIGN PATENT DOCUMENTS

EP    0469765    2/1992
JP    10135112    5/1998

OTHER PUBLICATIONS

Machine English Translation of Applicant's Admitted Prior Art: Japanese Patent 10135112 A, Oct. 9, 2008.*
Shiokawa, et al., In Situ Observation and Correction of Resist Patterns In Atomic Force Microscope Lithography, Applied Physics Letters, AIP, American Institute of Physics, vol. 72, No. 19, May 1998, pp. 2481-2843.
Milner, et al., Latent Image Exposure Monitor Using Scatterometry, Proceedings of the SPIE—The International Society for Optical Engineering USA, vol. 1673, 1992, pp. 274-283.
PCT International Search Report dated Jul. 4, 2007.

* cited by examiner

*Primary Examiner*—Thanh X Luu
*Assistant Examiner*—Francis M Legasse, Jr.
(74) *Attorney, Agent, or Firm*—McCarter & English, LLP

(57) ABSTRACT

An apparatus, system and method for targeting an image formed on an imaging member. The imaging member includes an imaging sensitive layer formed thereon. The imaging member includes imaged and non-imaged areas. Light of a predetermined wavelength reflected from a target area of the imaging member is received. The light reflected from the target area is representative of an image formed on the imaging sensitive layer using energy at approximately the predetermined wavelength. The predetermined wavelength is suitable to initiate crosslinking of the imaging sensitive layer.

46 Claims, 6 Drawing Sheets

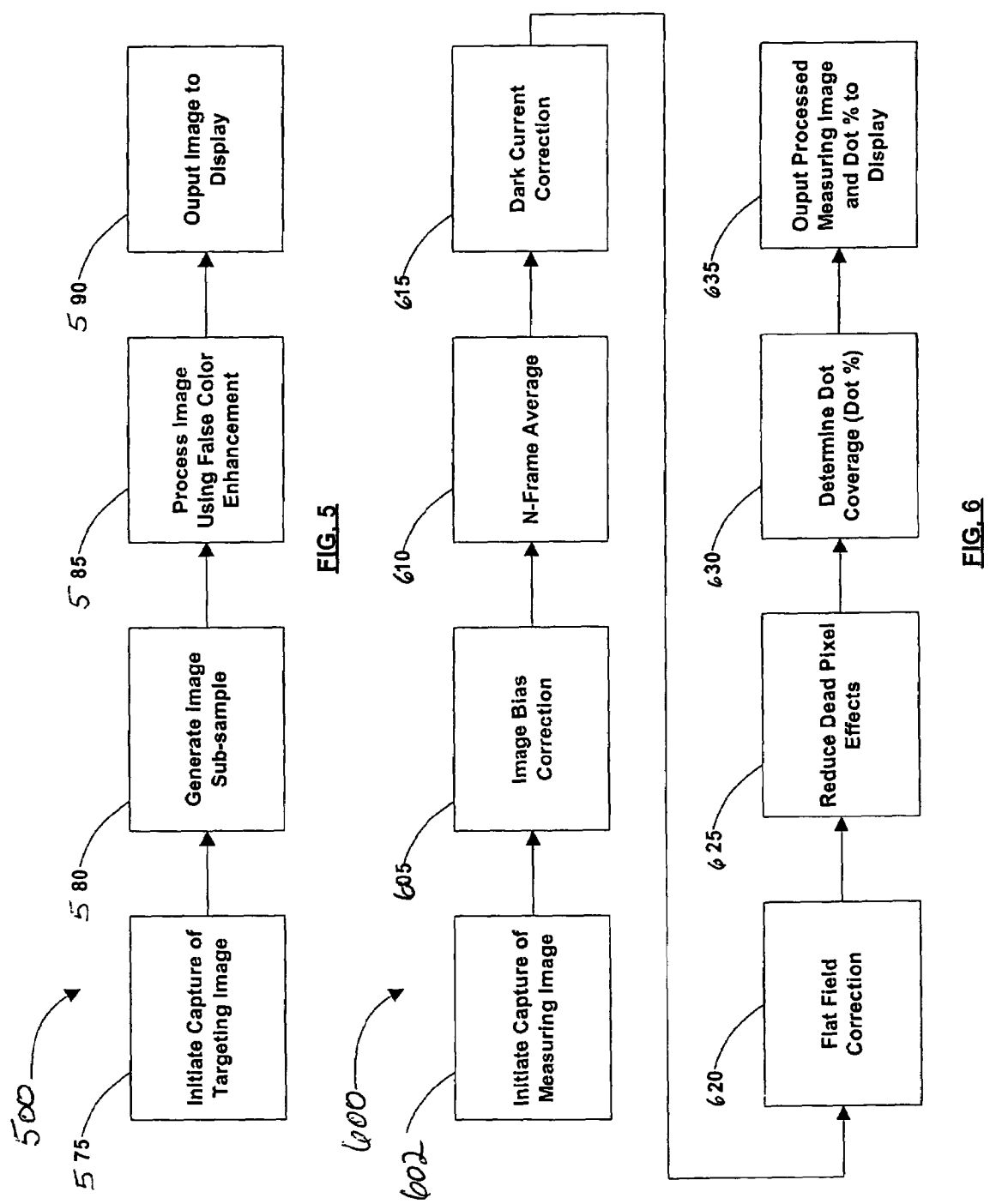

DEVICES AND METHODS FOR TARGETING PRINTING PLATES AND MEASURING DOT COVERAGE THEREON

PRIORITY

This application claims priority to U.S. Patent Application Ser. No. 60/715,117 entitled "METHOD OF TARGETING AND READING DOT COVERAGE ON 'PROCESSLESS' 'SEMI-LATENT IMAGE' CTP PRINTING PLATES" filed Sep. 8, 2005, and claims priority to U.S. Patent Application Ser. No. 60/788,899 entitled "DEVICES AND METHODS FOR TARGETING PRINTING PLATES AND MEASURING DOT COVERAGE THEREON" filed Apr. 3, 2006, the contents of both of these provisional applications is incorporated herein by reference in their entirety.

FIELD

Devices and methods for targeting an area of a printing plate and reading dot coverage of the targeted area.

BACKGROUND

Traditional printing technology, especially lithographic printing, employs printing plates to produce a printed image on a printing medium or substrate such as a paper. These printing plates may be produced with various imaging technologies such as computer-to-plate (CTP) or computer-to-film (CTF) imaging technology. In CTP imaging technology, an image to be printed may be created as a computer file and output directly to the printing plate. In CTF technology, the computer file representing the image is first output to a transparent film. The transparent film is then used to expose the printing plate. CTF technology is older. Modem printing processes increasingly use CTP technology because it removes a stage in the printing process. Regardless of the type of printing plate technology used, the image to be printed is rendered on the printing plate in the form of a pattern of "dots" having a predetermined density. The dots make up the printed image. Generally, one printing plate for each basic printing color (cyan, magenta, yellow and black) is employed to form the final printed full color image on the printing medium. Each different color printing plate will have a predetermined dot pattern thereon representing that color's contribution to the final full color image.

Traditional or "legacy" CTP printing plates have a high contrast between areas of exposure and non-exposure or, respectively, imaged and non-imaged portions of the printing plate. The high contrast may be achieved through diffuse illumination to provide uniform lighting of the medium to be measured, which may be referred to herein as a measurable medium and/or an imaging member, for example. Uniform lighting may be employed to better distinguish a suitable threshold setting between the exposed and non-exposed areas of the printing plate or imaged and non-imaged areas of the printing plate, respectively. The areas of interest on the CTP printing plates may be referred to as "targets" and the act of probing the target may be referred to as "targeting." The target may comprise image areas as well as non-image areas. In general, the target may be illuminated using a variety of illumination sources. The illumination sources for targeting may include red, green and blue (RGB) and white colored sources depending on the color of the CTP printing plate to be measured. Some devices for targeting the CTP printing plates may employ a physical reticule or targeting element configured for placement over or around a desired high contrast target for which dot coverage is to be measured. Measuring dot coverage may comprise, for example, measuring the size, spacing or angle of the dots that make up a printed image.

CTP printing plates utilize latent images. The latent image CTP printing plates may be referred to as "low-contrast," "processless" or "semi-latent image" printing plates. This type of CTP printing plate is referred to herein as latent image CTP printing plate. Latent images may not be readily visible to the naked eye and in some circumstances may be almost invisible, or completely invisible, to the naked eye. Methods for targeting latent image CTP printing plates that employ illumination sources in the visible spectrum to render the images "visible to the naked eye" are typically not successful or useful for targeting latent images on a latent image CTP printing plate because the user is unable to visualize or sight the latent image target area to measure the dot coverage on the target area. Therefore, it is difficult to sight a dot coverage test device, for example, over the target area of the printing plate to measure the size, spacing or angle of the dots that make up the printed image.

In view of the foregoing issues, there may be a need for improved methods, apparatuses and systems in various configurations for targeting, measuring and/or otherwise analyzing dot density or dot coverage on various measurable media including latent image CTP printing plates.

BRIEF DESCRIPTION OF THE FIGURES

The utility of the various embodiments described and illustrated herein will be readily appreciated and understood from consideration of the following description and accompanying drawings, wherein:

FIG. 5 is a block diagram of one embodiment of a logic flow, which may be implemented by one embodiment of the devices illustrated in FIGS. 1 and 4.

FIG. 6 is a block diagram of one embodiment of a logic flow, which may be implemented by one embodiment of the devices illustrated in FIGS. 1-4.

DESCRIPTION

Figure 1:
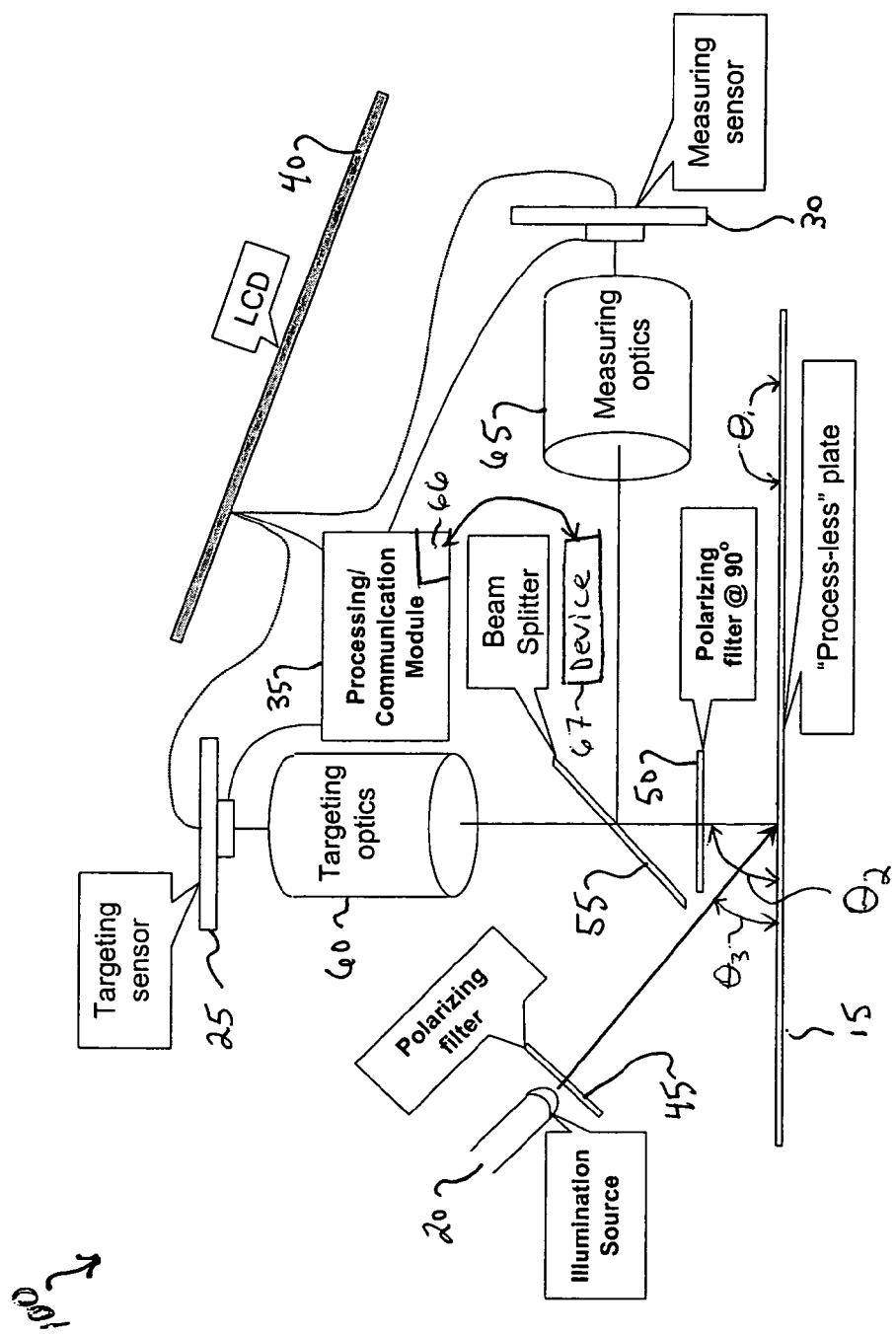
FIG. 1 illustrates a block diagram of one embodiment of a device to target a suitable imaging member.

Various embodiments of apparatuses, systems and methods for targeting, sighting and/or reading desired portions of an imaging member are disclosed. An imaging member may comprise any suitable measurable medium for rendering an image to be printed or for receiving a printed image. In various embodiments, an imaging member may comprise a support and one or more layers thereon that are sensitive to energy (e.g., heat, light, etc.) at a predetermined wavelength. The support may comprise any self-supporting material including polymeric films, glass, ceramics, metals or paper or a lamination of any of these materials. The one or more layers may be imaging sensitive layers that are spectrally sensitive to energy within a predetermined wavelength from the infrared to the ultraviolet, although the embodiments are not limited in this context. The imaging sensitive layer may be formed to absorb a specific dose of the energy at the predetermined wavelength to initiate crosslinking of the molecules forming the layer. The predetermined wavelength that initiates crosslinking will be referred to herein as the crosslinking wavelength. Areas of the imaging sensitive layer on the imaging member that are exposed to energy at the predetermined wavelength may be referred to herein as the image area and areas of the imaging sensitive layer that are not exposed to the energy at the predetermined wavelength may be referred to as the non-image area.

In one embodiment, an imaging member may be a printing plate comprising a metallic support and one or more spectrally sensitive imaging layers formed thereon. Printing plates may comprise various types of printing plates including offset printing plates. The term "printing plate" is used throughout this description to indicate any type of printing plate, including for example, processless printing plates, non-chemistry washed printing plates, semi-latent image CTP printing plates, conventional CTP printing plates and non-CTP printing plates, among others. Although not limited in this context, the embodiments described herein may be employed in targeting and reading any suitable imaging member comprising an image area formed by exposing a spectrally sensitive layer to energy at a predetermined wavelength. In one embodiment, the image area may be formed of dots to create a printed image on a suitable substrate. The imaging member may comprise non-image areas defined as those areas that are not exposed to energy at the predetermined wavelength. A target area may comprise image as well as non-image areas, for example.

In various embodiments, the imaging member may comprise images formed using various screening techniques. For example, amplitude modulation (AM), frequency modulation (FM) or stochastic, hybrid and/or cross-modulated (XM) screening techniques. In AM screening, the size of the constituent dots may vary based on tonal values. Larger dots render darker tonal values, or more saturated color, while smaller dots are used for lighter values. The dots are placed on a fixed grid, and the inks are applied at specified screen angles, creating the illusion of a continuous range of colors. In stochastic or FM screening, on the other hand, smaller dots of uniform size are used. To achieve darker or lighter tones the number of dots and their placement are modified. FM screening may sometimes be referred to as stochastic screening because the placement appears to be random, although dot placement is precisely controlled by sophisticated mathematical algorithms. In other screening techniques a printing plate may employ both the AM and FM screening techniques. These printing plates may be referred to as hybrid or XM plates.

Various embodiments provide a method of targeting and reading "processless" or "semi-latent image" digital printing CTP plates, for example, or printing plates of substantially similar design or structure. Embodiments may include methods for illuminating and displaying "processless" digital CTP plates and thus make the "invisible" target on the plates visible to the user. These embodiments allow targeting of what would be otherwise impossible to target with conventional methods.

Embodiments may further include apparatuses, systems and methods employing illumination techniques to illuminate an imaging member with light of the predetermined crosslinking wavelength used in rendering or forming the image area on the imaging member. The image area may be a latent or semi-latent image area. As used herein, a latent or semi-latent image area refers to an image area that is either invisible or nearly invisible to the naked, respectively. Detection techniques may be employed to detect light at the predetermined crosslinking wavelength reflected from the imaging member and render the image area visible when illuminated with light of the predetermined crosslinking wavelength to a display. The display may be a visual optical element, for example, or an electronic display device, such as a liquid crystal display (LCD) or cathode ray tube (CRT). Once the reflected light is detected, the image area formed on the imaging member may be displayed on the electronic display device or may be detected with the naked eye through the visual optical element. Thus, in one embodiment, the apparatuses, systems and methods employing the illumination and detecting techniques described herein may render "visible" latent target image areas formed on the imaging member that otherwise are "invisible" to the naked eye. Accordingly, the various embodiments enable targeting, sighting or displaying latent images that otherwise may not be readily visible or would be invisible to the naked eye.

The specular-excluded illumination of the "processless" digital CTP plate type imaging member provides a higher contrast for an optical display when the illumination is in the visible region of the electromagnetic wave spectrum. This specular-excluded illumination of the "processless" digital CTP plates also may provide a higher contrast when the excitation of the plate is in the radiometric regions that are invisible to the naked eye. The illumination may be captured with a detector that is capable of detecting the required radiometric frequencies and/or displaying the information on an electronic display that uses the RGB values to represent the otherwise invisible exposed and non-exposed areas (e.g., imaged and non-imaged areas) of the "processless" digital CTP plate.

Various embodiments may comprise apparatuses, systems and methods comprising one or more of the following features: targeting using a specular-excluded illumination source on "processless" digital CTP plates to increase contrast by making what is "invisible" visible; targeting using an optical element for display when the illumination is in the visible wavelength spectrum; targeting using an electronic detector and electronic display when the illumination is in the non-visible or visible wavelength spectrum; measuring using an electronic detector and electronic display when the illumination is in the non-visible or visible wavelength spectrum; displaying real-time target views or representations of the plate on an electronic display that enhances the image so that a user can see where the feature to be targeted is; using a specular-excluded chromatic illumination source with a frequency or wavelength approximately the same as or the same as the frequency or wavelength of a laser used to crosslink the polymer on the "processless" digital CTP plate in the platesetting machine; using a specular-excluded illumination source that can be interchanged or adjusted manually or automatically; porting a representative image in RGB format of the invisible "processless" plate to a computer or computer system; using polarized LED's as the source as well as sources transmitting through a polarizing filter; using the embodiments in embedded, inline and online applications with platesetting machines, for example. The following definitions may be applicable to the embodiments: "embedded" refers to the positioning of an instrument mounted inside a device (e.g., such as an OEM device); "inline" refers to the instrument being mounted externally with respect to the device; "online" refers to the instrument being mounted outside of and not on the device, but installed on the same process line as the device.

FIG. 1 illustrates a block diagram of one embodiment of a device 100 to target a suitable imaging member. The device 100 may be employed to target, read and measure dot coverage on a suitable imaging member such as a printing plate 15. For example, the device 100 may be employed to measure dot coverage such as, for example, to measure the size, spacing or angle of the dots that make up a printed image formed using AM, FM, hybrid and/or XM screening techniques, among others. The printing plate 15 may comprise a suitable spectrally sensitive imaging layer thereon. The imaging layer may be exposed to energy at a predetermined wavelength to initiate crosslinking of the molecules in the exposed areas to form an image area. The device 100 may comprise an illumination source 20, a targeting sensor 25, a measuring sensor 30, a processing/communication module 35 and a display 40. The device 100 also may comprise a first 90-degree-turned polarizing filter 45 for filtering light emitted by the illumination source 20, a second 90-degree-turned polarizing filter 50 for filtering light reflected from the printing plate 15 and a beam splitter 55 for directing light reflected from the printing plate 15 and passed through the second polarizing filter 55 to both the targeting sensor 25 and the measuring sensor 30. In one embodiment, the polarizing filter 45 and the illumination source 20 may be formed integrally as a single element or light source. In one embodiment, the polarizing filter 45 and the illumination source 20 may be interchangeable or replaceable whether formed integrally or as separate elements. The device 100 further may comprise targeting optic components 60 and measuring optic components 65 for processing light reflected from the printing plate 15 prior to it being received by the targeting and measuring sensors 25, 30, respectively. In various embodiments, the respective orientations of the measuring and targeting sensors 30, 25 may be approximately 0° ($\theta_1$) and 90° ($\theta_2$), respectively, relative to the printing plate 15, although the embodiments are not limited to these angular orientations as other suitable angular orientations may be employed. The illumination source 20 may be configured to generate light at or near the predetermined crosslinking wavelength to illuminate the printing plate 15. It will be appreciated by those skilled in the art that the wavelength of the light generated by the illumination source 20 may be at or approximately at the crosslinking wavelength. Therefore, the scope of the embodiments is not limited in this context. The light may be transmitted at an illumination angle $\theta_3$ formed between the illumination source 20 and the printing plate 15. In one embodiment, the illumination angle $\theta_3$ may be approximately 45° relative to the printing plate 15. Other suitable illumination angles $\theta_3$ may be used and the embodiments are not necessarily limited in this context.

According to various embodiments, the illumination source 20 may be implemented in any suitable manner. For example, the illumination source 20 may comprise a single light or multiple light sources. The illumination source 20 may be polarized or non-polarized. A polarized illumination source 20 may comprise a light source formed with an integral polarizing filter, for example. Each of the light sources may emit light in one or more wavelengths, including wavelengths in the visible or invisible spectrum. Multiple light sources may be arranged in one or more configurations. These configurations may comprise, for example, single or multiple linear arrays of light sources, a rectilinear arrangement (e.g., rectangular or square), a ring or solid circular arrangement, among others. In one embodiment, the illumination source may be implemented with multiple light sources arranged in a ring. The light sources may be configured for emitting light at one or more wavelengths and at one or more illumination angles $\theta_3$. In one embodiment, the light sources may be configured to generate light at one or more crosslinking wavelengths based on the type of spectrally sensitive imaging layer formed on the printing plate 15.

According to various embodiments, the illumination angle(s) $\theta_3$ of light emitted by the illumination source 20 may be adjustable. In one embodiment, for example, the illumination source 20 may comprise multiple light-emitting diodes (LED) attached to a flexible substrate that may be suitably deflected to produce a desired illumination angle(s) $\theta_3$. Such illuminator configurations are disclosed in provisional patent application Ser. No. 60/788,900 entitled "LIGHT SOURCE AND INSTRUMENTS INCLUDING SAME", which is incorporated herein by reference in its entirety.

Light at the crosslinking wavelength emitted by the illumination source 20 may be generated, for example, using an LED, although any suitable light source capable of emitting light at the crosslinking wavelength may be employed. The illumination source 20 may be formed as a wide spectral multi-point illumination source comprising multiple LEDs in any suitable arrangement. In one embodiment, the illumination source 20 may comprise multiple LEDs arranged in a ring configuration. The multiple LEDs may be selected to emit light at multiple wavelengths. In one embodiment, several LEDs may be arranged to emit light at the same wavelength while other LEDs emit light at a different wavelength and so on. Also, the LEDs may be spaced apart or arranged at various angles relative to each other. Evenly spaced LEDs may be arranged such that they are spectrally balanced, for example. The LEDs may emit light at one or more suitable crosslinking wavelengths based on the characteristics of the spectrally sensitive imaging layer.

Figure 7:
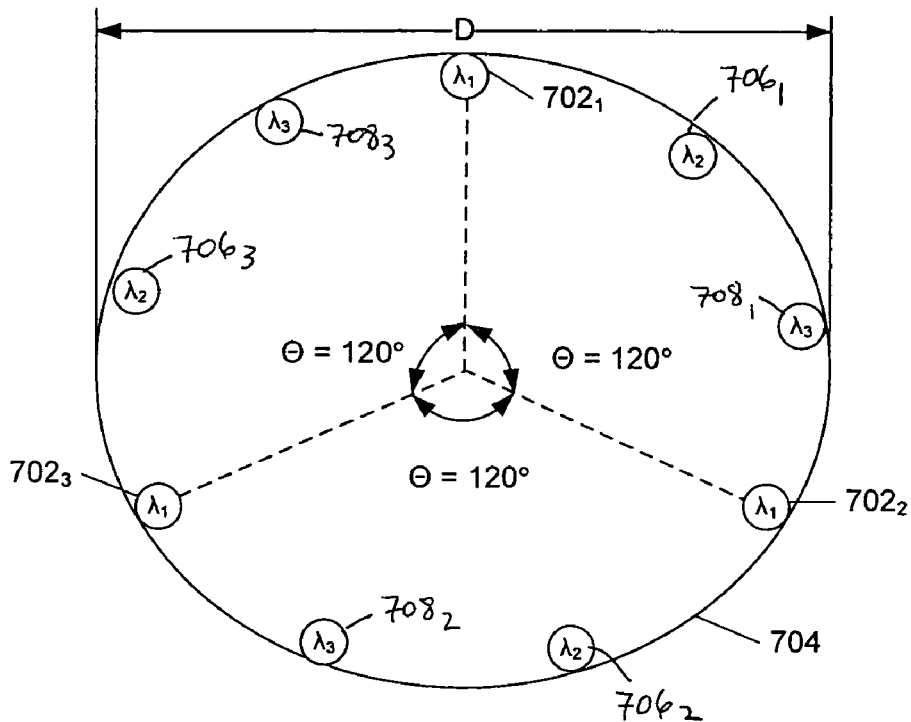
FIG. 7 illustrates one embodiment of an illumination source.

FIG. 7 illustrates one embodiment of an illumination source comprising an illumination ring 700 comprising multiple light sources 702, 706, 708 arranged in the form of a ring 704. For example, in one embodiment, the light sources 702, 706, 708 may be LEDs arranged in the form of a ring 704. In one embodiment, the illumination ring 700 may comprise three groups or banks of three light sources $702_{1-3}$, $706_{1-3}$, $708_{1-3}$ arranged in the ring 704 with a 120° separation angle between each of the three light sources in each group. Each group of light sources $702_{1-3}$, $706_{1-3}$, $708_{1-3}$ may emit light at a different wavelength $\lambda$. For example, light sources $702_{1-3}$ are arranged at a 120° separation angle between them and emit light at a first wavelength $\lambda_1$; light sources $706_{1-3}$ are arranged at a 120° separation angle between them and emit light at a second wavelength $\lambda_2$; and light sources $708_{1-3}$ are arranged at a 120° separation angle between them and emit light at a third wavelength $\lambda_3$. It will be appreciated that additional LEDs may be arranged in the ring 704 at a separation angle of 120°. In various other embodiments, the illumination ring 700 comprises comprise n light sources or groups of light sources (where n is any integer) arranged in the ring 704 configuration that emit light at n different wavelengths $\lambda_n$. For example, the illumination ring 700 may comprise twenty LEDs grouped into five banks of four LEDs each, where the LEDs in each bank are spaced at approximately 90° from each other. In one embodiment, the multiple light sources 702 (e.g., LEDs) each may emit light of the same wavelength or may emit light at different wavelengths, e.g., $\lambda_1$, $\lambda_2$ and/or $\lambda_3$, which include multiple crosslinking wavelengths. In one embodiment, the diameter D of the illumination ring 700 may be selected to be sufficiently large so as not to interfere with the field of view of the targeting sensor 25 and the targeting optics 60, for example. In one embodiment, the geometry and orientation of the illumination ring 700 may be configured to generate a uniform illumination spot on the imaging member (e.g., the printing plate 15). The area illuminated by the illumination spot may be referred to as a target area, for example. If the target comprises a crosslinked portion of the imaging layer, the target area may be referred to as an image target area. In one embodiment, the illumination ring 700 may be formed to provide an illumination spot on the imaging member that may be uniform to approximately 10% across a diameter of approximately 3 mm.

The wavelengths $\lambda_1$, $\lambda_2$ and/or $\lambda_3$ of the light emitted by one or more of the light sources 702, 706, 708 (e.g., LEDs) may be selected to enhance the contrast of the image target area relative to the non-image target area of the imaging member. For example, in one embodiment, the wavelengths of the light emitted by the one or more of the light sources 702 may be selected to optimally enhance the contrast of latent images formed on the image area relative to the non-image area formed on the imaging member (e.g., the printing plate 15). In one embodiment, the wavelengths of the light emitted by the one or more of the light sources 702 may be the crosslinking wavelengths. Additionally, specular-excluded light reflected from the printing plate 15 may provide a higher contrast to optically display the target image area when the wavelengths are in the visible region of the electromagnetic wave spectrum. The reflected light also may provide a higher contrast when the wavelengths are in the invisible (e.g., infrared) region of the electromagnetic wave spectrum.

With reference back to FIG. 1, in one embodiment, the illumination source 20 may comprise a light source similar to the illumination ring 700. The light source may comprise one or more LEDs that emit wavelengths in the visible spectrum, invisible spectrum or a combination thereof. For example, the light source may emit wavelengths in any one of the visible spectrum of approximately 405, 470, 520 and 630 nm; and in the invisible spectrum of approximately 830 nm. In one embodiment, a light source may be polarized or non-polarized. A polarized light source may comprise an LED integrally formed with a polarizing filter to emit polarized light. It will be appreciated that any wavelengths in the visible or invisible spectrum suitable for crosslinking the spectrally sensitive imaging layer may be utilized. Additionally, it will be appreciated that the number of banks, the number of LEDs in each bank, as well as the orientation of the banks within the illumination source 20 may be varied or modified as needed. The brightness and power dissipation of the LEDs may be individually controlled using known pulse-width modulation techniques among others. The LEDs may be energized in any suitable manner and in any combination using control logic such as, for example, programmable control logic. According to various embodiments, the control logic may be contained within a field-programmable gate array (FPGA) or other suitable programmable medium integral to the device 100, such as a processor or other computing device.

In various embodiments, additional contrast enhancing may be provided by matching the wavelength emitted by the illumination source 20 with the wavelength of a laser used in a platesetter to crosslink a polymer on the printing plate 15 or other imaging member. To address the existence of different printing plate types which may have different crosslinking wavelengths in the platesetter, embodiments may include the capability to manually and/or automatically adjust or replace the illumination source 20 to match the particular crosslinking wavelength of each different printing plate type.

According to various embodiments, the beam splitter 55 may be implemented using a half-silvered mirror or other suitable optical device for re-distributing light reflected from the printing plate 15 to the targeting and measuring optics 60, 65, respectively. In one embodiment, the beam splitter 55 may be characterized by an 80/20 configuration wherein approximately 20% of the received light reflected from the printing plate is directed to the targeting optics 60 and approximately 80% of the received light reflected from the printing plate is directed to the measuring optics 65. It will be appreciated, however, that the beam splitter 55 may be configured to distribute the light reflected from the printing plate 15 in accordance with any suitable distribution ratio. Therefore, the embodiments are not limited in this context.

The targeting and measuring optics 60, 65, respectively, may comprise one or more optical components for suitably processing the light reflected from the printing plate 15 prior to its being received by the targeting and measuring sensors 25, 30, respectively. Such components may include, for example, an aperture and/or a shutter for controlling the amount of light passed to the respective targeting and measuring sensors 25, 30 and one or more lenses for controlling field of view.

According to various embodiments, the targeting sensor 25 may be implemented using a Complimentary Metal Oxide Semiconductor (CMOS) or a Charge Coupled Device (CCD) digital camera for receiving the light reflected from the printing plate 15 via the targeting optics 60. The targeting sensor 25 generates images corresponding to the images on the target area of the imaging member or measurable medium such as the printing plate 15. In one embodiment, the targeting sensor 25 may comprise a CMOS color camera having a suitable resolution and output format. For example, the targeting sensor 25 may be a CMOS color camera having 640×480 pixel resolution and a VGA output format.

According to various embodiments, the measuring sensor 30 may be implemented using a CMOS or CCD digital camera for receiving the light reflected from the target area via the measuring optics 65. The measuring sensor 30 generates images corresponding to the images on the printing plate 15. In one embodiment, the measuring sensor 30 may comprise a CMOS monochrome camera having a suitable resolution. For example, the measuring sensor 30 may be a CMOS monochrome camera having a 1.3 mega pixel resolution and an 8 or 10-bit pixel resolution (i.e., 256 or 1024 gray scale levels per pixel, respectively). In one embodiment, the measuring optics 65 or the measuring sensor either individually or in combination may magnify the portion of the light reflected from the printing plate 15 to reveal the underlying dot structure or dot pattern such as, for example, the size, spacing and angle of the dots formed on the target area of the printing plates being illuminated.

The processing/communication module 35 (e.g., processor) may be adapted to capture images from the targeting sensor 25 and/or the measuring sensor 30. The processing/communication module 35 may then display the captured images on the display 40, such as the LCD display. The processing/communication module 35 also may be adapted to receive and process information whether from an external device or a user. The processing/communication module 35 also may be adapted to transmit information to an external device or a user. In one embodiment, the processing/communication module 35 may comprises an interface 66 to communicate using any suitable protocol. The interface 66 may be a wired or wireless interface. In various embodiments, the interface 66 may be a wired or wireless universal serial bus (USB) type interface. In various embodiments, the images captured by the device 100 may be ported to an external processing device 67 via the interface 66. Examples of the external processing device 67 may comprise a computer, an inline digital platesetting machine, an embedded digital platesetting machine or any suitable external processing device that may utilize the output of the device 100.

Figure 2:
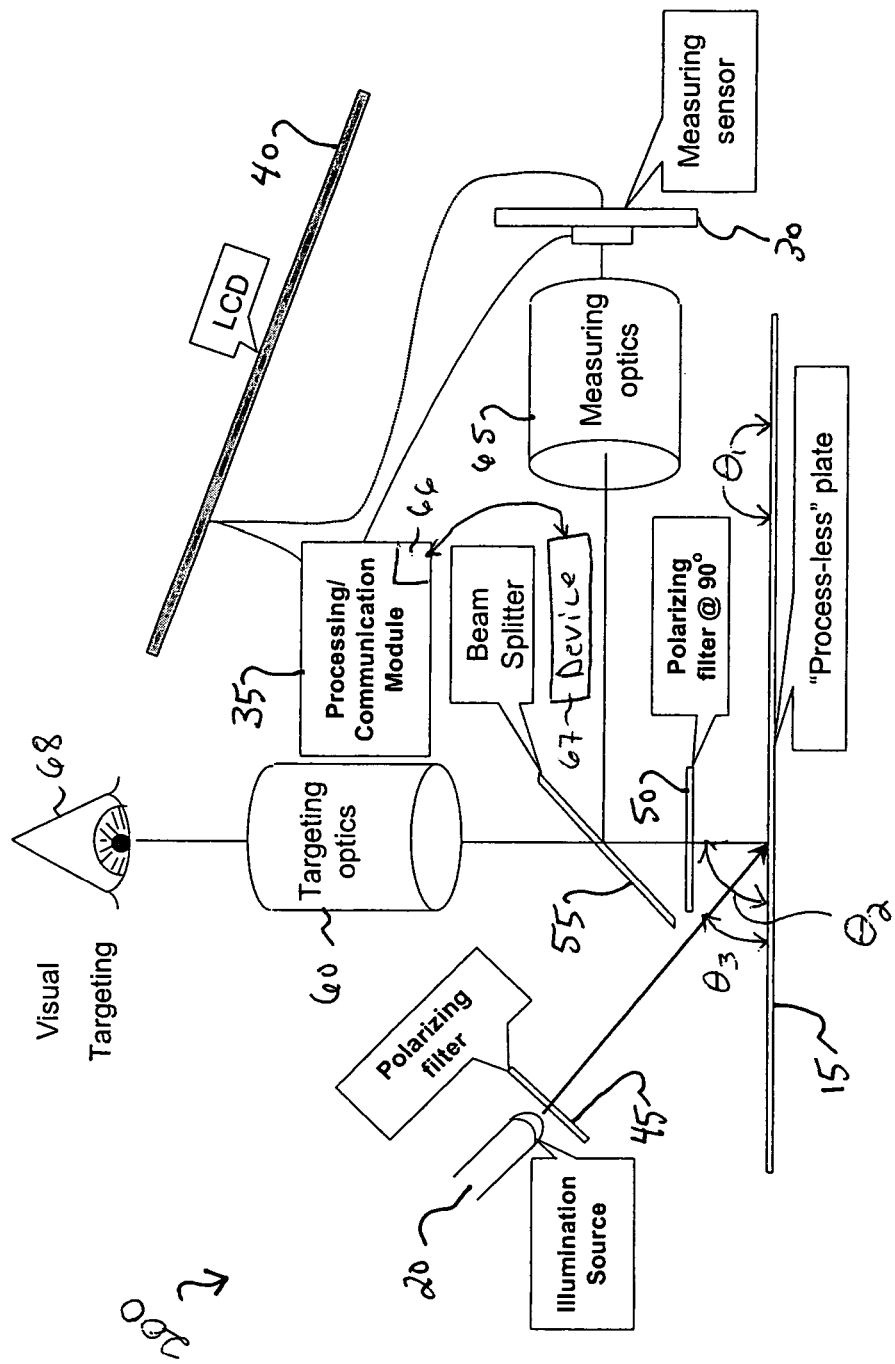
FIG. 2 illustrates one embodiment of a device to target a suitable imaging member.

FIG. 2 illustrates one embodiment of a device 200 to target a suitable imaging member. The device 200 may be employed to target, read and measure dot coverage on a suitable imaging member such as the printing plate 15. The device 200, however, does not include the targeting sensor 25. Rather, the embodiments of the device 200 illustrated in FIG. 2 may be employed to determine the dot coverage or dot percentage values for the printing plate 15 implemented as a conventional or CTP printing plate containing images that are visible to the naked eye 68. In one such embodiment, the device 200 may be configured in a manner similar to that of the device 100 illustrated in FIG. 1, with the exception that the targeting sensor 25 is removed such that visual targeting using the naked eye 68 through the targeting optics 60 may be employed.

Figure 3:
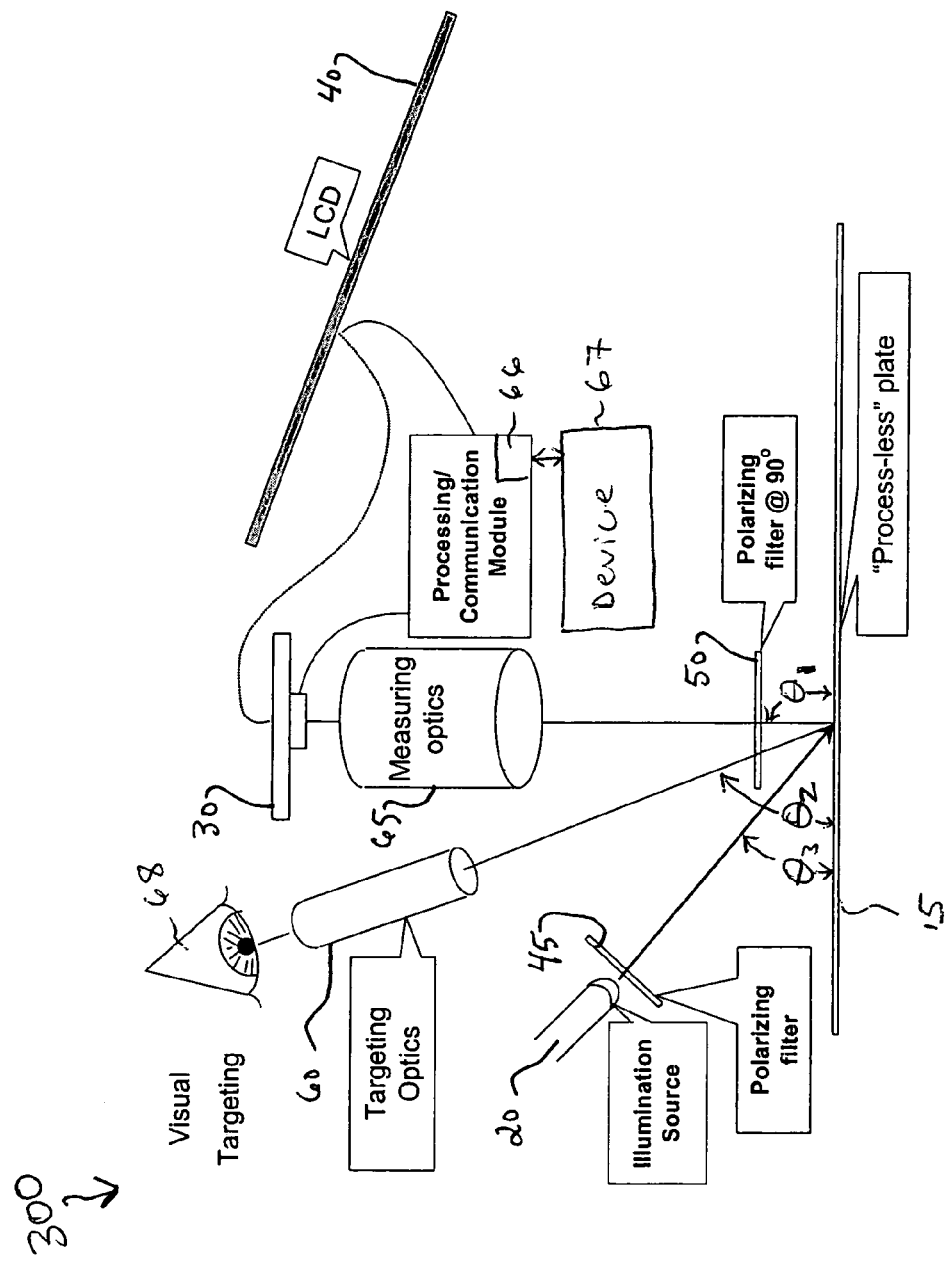
FIG. 3 illustrates one embodiment of a device to target a suitable imaging member.

FIG. 3 illustrates one embodiment of a device 300 to target a suitable imaging member. The device 300 may be employed to target, read and measure dot coverage on a suitable imaging member such as the printing plate 15. In the device 300, however, the beam splitter 55 (shown in FIGS. 1 and 2) and the targeting sensor 25 (shown in FIGS. 1, 2 and 4) have been removed. Further, the measuring optics 65 and the measuring sensor 30 may be oriented at 90°$\theta_1$ with respect to the printing plate 15. Accordingly, the visual targeting may be performed by orienting the targeting optics 60 at an acute angle $\theta_2$ with respect to the printing plate 15.

Figure 4:
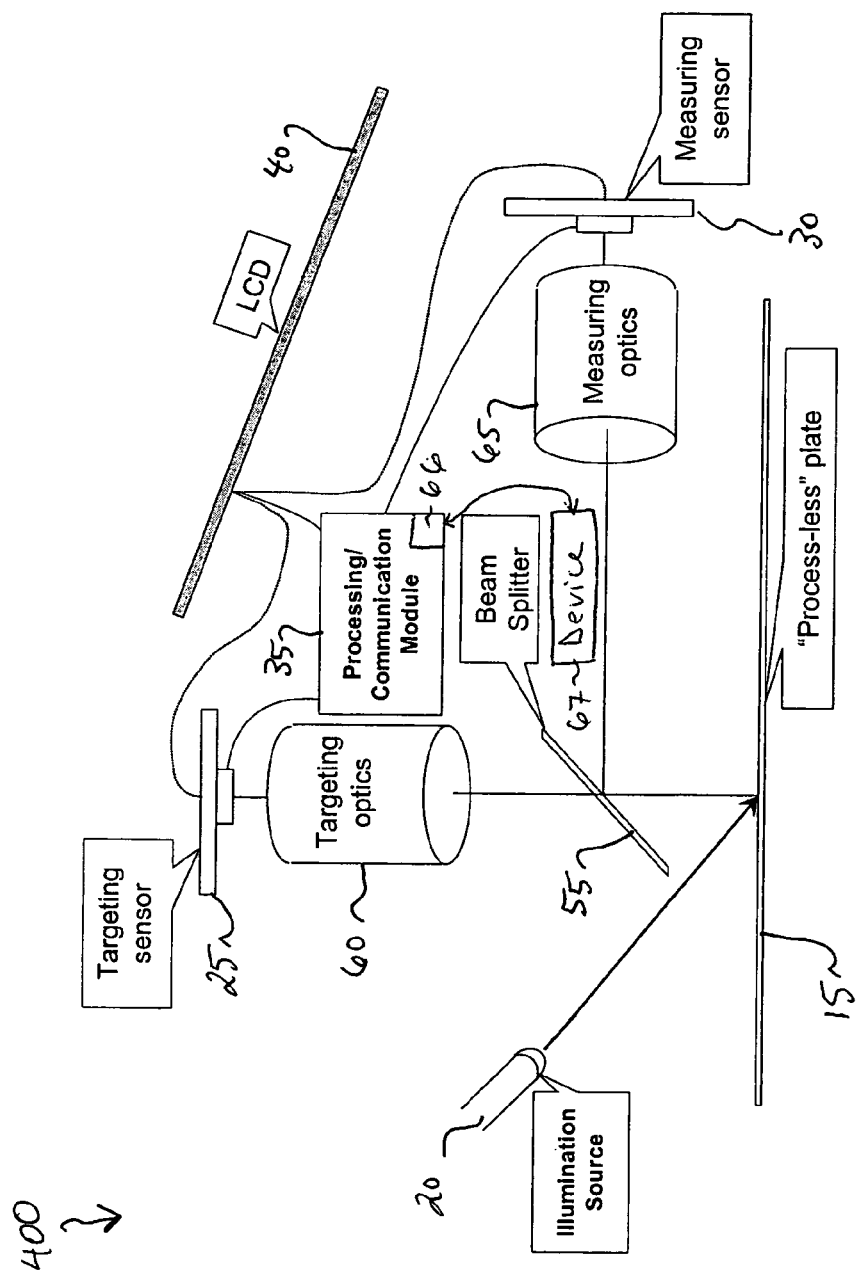
FIG. 4 illustrates one embodiment of a device to target a suitable imaging member.

FIG. 4 illustrates one embodiment of a device 400 to target a suitable imaging member. The device 400 may be employed to target, read and measure dot coverage on a suitable imaging member such as the printing plate 15. In the device 400, however, the polarizing filters 45, 55 as shown in FIGS. 1-3, for example, are removed. According to various embodiments, one or more of the polarizing filters 45, 55 depicted in any of the embodiments of FIGS. 1-3 also may be removed.

FIG. 5 is a block diagram of one embodiment of a logic flow 500, which may be implemented by one embodiment of the device 100 or 400. The logic flow 500 will be described with reference to the device 100, although the same principles may be applied to the device 400. Image capture by the targeting sensor 25 may be controlled internally and/or by the processing/communication module 35 responsive to input commands provided by a user of the device 100 or by an external input from an external device that may be received from the interface 66. In addition, input commands also may be provided by a user interface. In one embodiment, for example, the input commands may be provided via a graphical user interface implemented by the processing/communication module 35 and the display 40.

At blocks 575, image capture by the targeting sensor 25 may be initiated in response to a user input. According to various embodiments, the targeting sensor 25 may automatically implement one or more default image capture settings when activated. Certain image capture settings such as color balance, however, may need to be adjusted using histogram equalization, for example.

At block 580, captured images may be processed to generate corresponding image sub-samples having pixel sizes compatible with the display 40. Such processing may comprise, for example, performing VGA to ¼ VGA conversions. To increase the speed with which the image sub-samples are generated, processing may be implemented using instructions stored within a field programmable gate array (FPGA) integral to the targeting sensor 25.

At block 585, captured images may be further processed to provide false color enhancement and improved contrast using, for example, a false color look-up table or calorimetric histogram-based mapping techniques. Such processing may be implemented by instructions stored within an FPGA integral to the device 100.

At block 590, processed images may be output to the display 40 for viewing. The display 40 may comprise, for example, a color LCD screen or other display device suitable for viewing the processed images. According to various embodiments, targeting images may be captured and processed in a continual fashion. Thus, as the device 100 is moved across the printing plate 15, the display 40 may be automatically updated in real-time as new images are acquired. In other embodiments, the display may be manually updated responsive to user input. The use of an illumination source 20 employing visible and invisible crosslinking wavelengths for illuminating the printing plate 15, as well as the use of false color enhancement or histogram-based mapping for processing captured images, enables the user to view otherwise latent or semi-latent image areas on the printing plate 15 via the display 40. Any images on the printing plate 15 for which dot coverage is to be determined (e.g., measured), including latent and semi-latent images, may be visualized via the display 40.

FIG. 6 is a block diagram of one embodiment of a logic flow 600, which may be implemented by one embodiment of the devices 100, 200, 300, 400 in accordance with one embodiment of the logic flow 500 as illustrated in FIG. 5. At block 602, image capture by the measuring sensor 30 may be initiated in response to a user input or to an input received from an external device. Various image processing algorithms may be utilized to correct image imperfections resulting from inherent limitations of the measuring sensor 30. The algorithms may be implemented, for example, using corresponding logic instructions stored within the processing/communication module 35. At block 605, captured images may be processed using a suitable bias correction algorithm to subtract effects (e.g., offset, shading) introduced to the image data by the measuring sensor 30. The appropriate bias correction may be pre-determined and configured during factory calibration of the device 100. At block 610, random noise appearing in the captured images may be reduced by averaging N image frames. At block 615, the captured images may be processed using a dark current correction algorithm such that effects due to dark current noise are subtracted from the images. Dark current correction may be performed, for example, during process calibration. At block 620, the captured images may be processed using a flat field correction algorithm to reduce variation between adjacent pixels. Flat field correction may be performed, for example, during field calibration of the device 100. At block 625, dead pixels within the measuring sensor 25 may be mapped and their effects reduced using nearest neighbor substitution or interpolation algorithms.

The processing/communication module 35 may process the image at block 630 to determine its dot coverage. According to various embodiments, the determined dot coverage may be expressed in terms of a dot percentage (%) value. At block 635, a magnified view of the measuring image showing the dots, along with the dot percentage, may be output to the display 40.

As noted above, the device 100 may comprise a graphical user interface implemented using the processing/communication module 35 and the display 40. According to various embodiments, the graphical user interface may be programmed using any suitable programming tool and may support four general modes of operation: calibration, measurement, configuration and analysis. In the calibration mode, one or more calibration routines for calibrating the instrument may be executed. Information relating to instrument calibration may communicated from the device 100 to an external device (e.g., a PC) via a suitable communication link (e.g., USB port, serial port, etc.) supported by the processing/communication module 35, such as the interface 66. In various embodiment, the communications link may be wired or wireless. The communication link also may be used to communicate calibration information from the external device to the device 100. The configuration mode may enable the setup of one or more instrument connection parameters and control parameters for controlling device operation using, for example, a suitable device communication layer. In the measurement mode, measurement routines may be executed for requesting measurement sets and images for communication to the display 40. In the analysis mode, analysis routines may be executed, for example, to view one or more measurement sets on a graph corresponding to the dot profile of the printing plate 15 from which the measurement set(s) were obtained. Measurement sets and images may be tagged with information such as, for example, the printing plate 15 from which the measurement and image data originated, the press in which the printing plate 15 is used and the configuration of the press. Additionally, the measurement sets and images may be saved to files internal to the device 100 and recalled as needed. Still further, the measurement sets and images may be transferred to the external device (e.g., a PC) via the communication link by way of the interface 66. Other operational modes, as well as other features and functions may be incorporated in other embodiments of the device 100.

Figure 8:
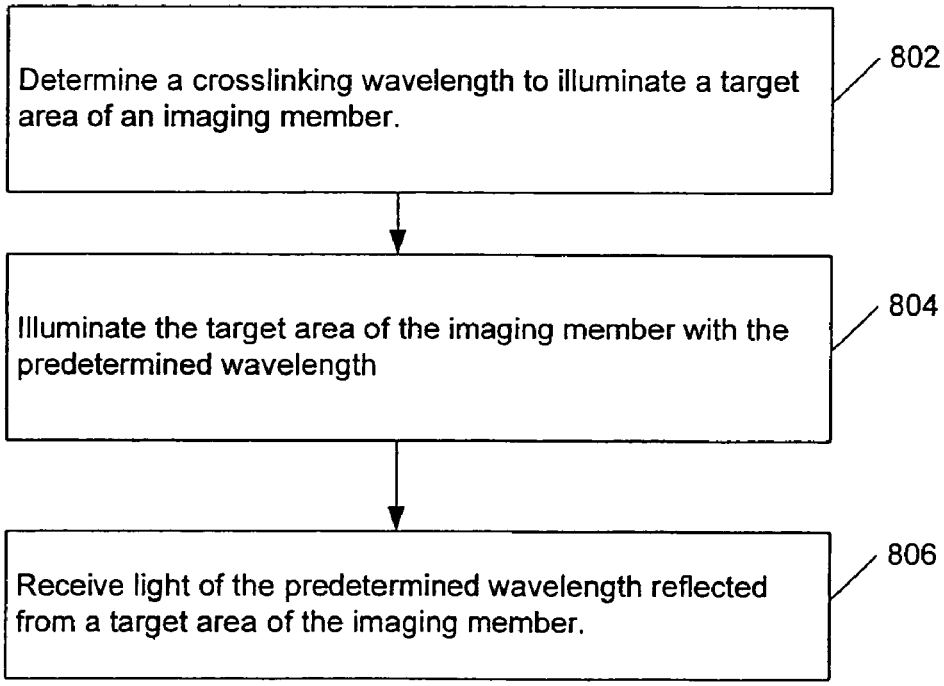
FIG. 8 is a block diagram of one embodiment of a logic flow.

FIG. 8 is a block diagram of one embodiment of a logic flow 800. At block 802, a crosslinking wavelength is determined to illuminate a target area of the imaging member. It will be appreciated by those skilled in the art that the predetermined crosslinking wavelength may be the approximate value of the actual crosslinking wavelength used to crosslink the imaging sensitive layer of the imaging member. The predetermined crosslinking wavelength renders visible the image area relative to the non-image area of the on the imaging member (e.g., the printing plate 15). At block 804, the target image area is illuminated with the predetermined crosslinking wavelength. At block 806, the device 100 receives light of the predetermined wavelength reflected from a target area of the imaging member. The imaging member comprises an imaging sensitive layer formed thereon. The light reflected from the target area is representative of an image formed on the imaging sensitive layer using energy at the predetermined wavelength. The predetermined wavelength is suitable to initiate crosslinking of the imaging sensitive layer. The targeting sensor 25 receives a first portion of light reflected from the target area of the imaging member. The first portion of the reflected light having the predetermined crosslinking wavelength. The reflected light is representative of a target image formed on the target image area of the imaging member. The predetermined wavelength is selected to be the crosslinking wavelength to render the target image area detectable either by the targeting sensor 25 or the naked eye. In one embodiment, the crosslinking wavelength may enhance the contrast of the image area relative to the non-image area of the imaging member. In various embodiments, the logic flow 800 may be adapted to capture the target image represented by the first portion of the reflected light with a digital camera (e.g., CMOS or CCD camera) formed integrally with or in addition to the targeting sensor 25. Additionally, the captured target image may be displayed on the display 40. Furthermore, the predetermined crosslinking wavelength may be in any one of a visible and invisible spectrum. In various embodiments, for example, the crosslinking wavelength may be any one of a 405 nm, 470 nm, 520 nm, 630 nm and 830 nm, among other suitable crosslinking wavelengths. The target image area on the imaging member may comprise latent, semi-latent and/or non-latent images thereon.

As described with reference to the logic flow 500 in FIG. 5, the device 100 may generate a target image sub-sample having a predetermined pixel size. In addition, the target image may be enhanced to improve the contrast using false color enhancement. For example, the target image may be enhanced using any one of a false color look-up table mapping technique. In one embodiment, a colorimetric histogram-based mapping technique may be employed, for example.

In one embodiment, the logic flow 800 may be adapted to receive a second portion of the light reflected from the target image area of the imaging member at the measuring sensor 30. The second portion of the reflected light also has the predetermined crosslinking wavelength. The reflected light is representative of the image formed on the target image area of the imaging member. In addition, the second portion of the reflected light may be magnified to reveal an underlying dot structure of the detected target image area. Further, the magnified measure image area represented by the second portion of the reflected light may be captured by a digital camera (e.g., CMOS or CCD camera) formed integrally with or in addition to the measuring sensor 30. The captured measure image may be displayed on the display 40 device. The display 40 may present either the target image or the measure image in response to an external input. The external input may be received from a user or from an external device. The dot coverage of the measure image may be computed and presented on the display 40.

In addition, the logic flow 800 may be adapted to process the captured measure image to correct the captured measure image bias; average a predetermined number of the captured measure image frames; subtract dark current noise from the captured measure image; reduce variations between adjacent pixels of the captured measure image; and map dead pixels in the captured measure image and substituting the mapped dead pixels with near neighboring pixels or interpolated pixels.

The examples presented herein are intended to illustrate potential and specific implementations of the various embodiments described herein. It can be appreciated that the examples are intended primarily for purposes of illustration for those skilled in the art. No particular aspect or aspects of the examples is/are necessarily intended to limit the scope thereof.

It is to be understood that the figures and descriptions have been simplified to illustrate elements that are relevant for a clear understanding of the various embodiments, while eliminating, for purposes of clarity, other elements. Those of ordinary skill in the art will recognize, however, that these and other elements may be desirable. However, because such elements are well known in the art and because they do not facilitate a better understanding of the embodiments, a discussion of such elements is not provided herein.

Any element expressed herein as a means for performing a specified function is to encompass any way of performing that function including, for example, a combination of elements that perform that function. Furthermore, functionalities provided by the various recited means may be combined and brought together in a manner as defined by the appended claims. Therefore, any means that can provide such functionalities may be considered equivalents to the means shown herein.

In general, it will be apparent to one of ordinary skill in the art that various embodiments described herein may be implemented in, or in association with, many different embodiments of software, firmware and/or hardware. The actual software code or specialized control hardware used to implement some of the present embodiments is not indented to limit the scope of the embodiments. For example, certain aspects of the embodiments described herein may be implemented in computer software using any suitable computer software language type such as, for example, C or C++ using, for example, conventional or object-oriented techniques. Such software may be stored on any type of suitable computer-readable medium or media such as, for example, a magnetic or optical storage medium. Thus, the operation and behavior of the embodiments may be described without specific reference to the actual software code or specialized hardware components. The absence of such specific references is feasible because it is clearly understood that artisans of ordinary skill would be able to design software and control hardware to implement the various embodiments based on the description herein with only a reasonable effort and without undue experimentation.

Moreover, the processes, systems and devices associated with the present embodiments may be executed by, or in operative association with, programmable equipment, such as computers and computer systems. Software that cause programmable equipment to execute the processes may be stored in any storage device, such as, for example, a computer system (non-volatile) memory, an optical disk, magnetic tape, or magnetic disk. Furthermore, the processes may be programmed when the computer system is manufactured or via a computer-readable medium. Such a medium may include any of the forms listed above with respect to storage devices and may further include, for example, a carrier wave modulated, or otherwise manipulated, to convey instructions that may be read, demodulated/decoded and executed by a computer.

It can also be appreciated that certain process aspects described herein may be performed using instructions stored on a computer-readable medium or media that direct a computer system to perform the process aspects. A computer-readable medium may include, for example, memory devices such as diskettes, compact discs of both read-only and read/write varieties, optical disk drives and hard disk drives. A computer-readable medium may also include memory storage that may be physical, virtual, permanent, temporary, semi-permanent and/or semi-temporary. A computer-readable medium may further include one or more data signals transmitted on one or more carrier waves.

A "computer" or "computer system" may be, for example, a wireless or wireline variety of a microcomputer, minicomputer, server, mainframe, laptop, personal data assistant (PDA), wireless e-mail device (e.g., "BlackBerry" trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include any means for storing software, including a hard disk, an optical disk, floppy disk, ROM (read only memory), RAM (random access memory), PROM (programmable ROM), EEPROM (electrically erasable PROM) and other computer-readable media.

In various embodiments disclosed herein, a single component may be replaced by multiple components, and multiple components may be replaced by a single component, to perform a given function or functions. Except where such substitution would not be operative to practice the embodiments, such substitution is within the scope of the embodiments.

While various embodiments have been described herein, it should be apparent that various modifications, alterations and adaptations to those embodiments may occur to persons skilled in the art. The disclosed embodiments are therefore intended to include all such modifications, alterations and adaptations without departing from the intended scope.

The invention claimed is:

1. A method, comprising:
receiving light of a predetermined wavelength reflected from a target area of an imaging member, the imaging member comprising an imaging sensitive layer formed thereon, wherein the light reflected from the target area is representative of an image formed on the imaging sensitive layer using energy at approximately the predetermined wavelength, wherein the predetermined wavelength is suitable to initiate crosslinking of the imaging sensitive layer, wherein a first portion of the received light comprises a target image and is received at a targeting sensor, generating a target image sub-sample having a predetermined pixel size; and enhancing the target image to improve contrast using false color enhancement from values provided in a false color look-up table.

2. The method of claim 1, comprising:
receiving the target image at a visual optical element.

3. The method of claim 2, comprising:
passing the target image through a polarizing filter.

4. The method of claim 1, comprising:
receiving the target image at an electronic display device; and
displaying the target image on the electronic display device.

5. The method of claim 1, comprising:
illuminating the target area with polarized light from an illumination source through a first polarizing filter interposed between the imaging member and the illumination source.

6. The method of claim 5, comprising:
passing the target image through a second polarizing filter interposed between the imaging member and the targeting sensor.

7. The method of claim 1, comprising:
receiving a second portion of the received light at a measuring sensor, wherein the second portion of the received light comprises a measure image.

8. The method of claim 7, comprising:
magnifying the measure image to visually render an underlying dot structure of the measure image on a display device.

9. The method of claim 8, comprising:
capturing the magnified measure image.

10. The method of claim 7, comprising:
receiving a target image at a targeting sensor; and displaying either the target image or the measure image in response to an external input.

11. The method of claim 7, comprising:
computing dot coverage of the measure image; and
displaying the dot coverage.

12. The method of claim 7, comprising:
processing the measure image using any of one of the following:
correcting measure image bias;
averaging a predetermined number of measure image frames;
subtracting dark current noise from the measure image;
reducing variations between adjacent pixels of the measure image; and
mapping dead pixels in the measure image and substituting the mapped dead pixels with near neighboring pixels or interpolated pixels.

13. The method of claim 7, comprising:
passing the measure image through a polarizing filter.

14. The method of claim 1, wherein the predetermined wavelength is a wavelength in any one of a visible and invisible spectrum.

15. The method of claim 1, wherein the imaging member comprises any one of a latent and non-latent image.

16. An apparatus to target an image formed on an imaging member, the apparatus comprising:
a measure sensor to receive a first portion of light of a predetermined wavelength reflected from a target area of an imaging member, the imaging member comprising an imaging sensitive layer formed thereon,
a target sensor to receive a second portion of the reflected light from the target area of the imaging member said second portion of the reflected light comprising a target image, and
a processor adapted to generate a target image sub-sample having a predetermined pixel size; and enhance the target image to improve the contrast using false color enhancement from values provided in a false color look-up table,
wherein the first portion of the reflected light from the target area is representative of an image formed on the imaging sensitive layer using energy at approximately the predetermined wavelength,
wherein the predetermined wavelength is suitable to initiate crosslinking of the imaging sensitive layer.

17. The apparatus of claim 16, comprising:
an illumination source to illuminate the target area of the imaging member with light having the predetermined wavelength.

18. The apparatus of claim 17, wherein the illumination source is interchangeable with another illumination source to emit energy at approximately another predetermined wavelength suitable to initiate crosslinking of the imaging sensitive layer.

19. The apparatus of claim 17, comprising:
a processor coupled to the measure sensor to capture a measure image represented by the first portion of the reflected light.

20. The apparatus of claim 16, comprising:
at least one measure optic component interposed between the imaging member and the measure sensor to process the first portion of the reflected light before the measure sensor receives the first portion of the reflected light.

21. The apparatus of claim 16, comprising:
at least one target optic component interposed between the imaging member and the target sensor to process the second portion of the reflected light before the target sensor receives the second portion of the reflected light.

22. The apparatus of claim 16, comprising:
a first filter interposed between the imaging member and an illumination source to polarize the light emitted from the illumination source.

23. The apparatus of claim 22, wherein the first filter is formed integrally with the illumination source.

24. The apparatus of claim 23, wherein the illumination source is a polarizing light-emitting diode.

25. The apparatus of claim 22, comprising:
a second filter interposed between the imaging member and the target sensor to polarize the light reflected from the imaging member.

26. The apparatus of claim 16, comprising:
a beam splitter interposed between the imaging member and the target sensor to split the light reflected from the imaging member in two separate paths.

27. The apparatus of claim 16, comprising:
a display coupled to the processor to display either the target image or the measure image in response to an external input.

28. The apparatus of claim 16, further comprising an illumination source that comprises:
one or more light sources to emit light at the predetermined wavelength.

29. The apparatus of claim 28, wherein the one or more light sources emit light at any of a visible and invisible spectrum.

30. The apparatus of claim 28, wherein the target area of the imaging member comprises any one of a latent and non-latent image.

31. A system to target an image formed on an imaging member, the system comprising:
a measure sensor to receive a first portion of light of a predetermined wavelength reflected from a target area of an imaging member, the imaging member comprising an imaging sensitive layer formed thereon,
wherein the first portion of reflected light from the target area is representative of an image formed on the imaging sensitive layer using energy at approximately the predetermined wavelength,
wherein the predetermined wavelength is suitable to initiate crosslinking of the imaging sensitive layer,
a target sensor to receive a second portion of the reflected light from the target area of the imaging member said second portion of the reflected light comprising a target image,
a processor adapted to generate a target image sub-sample having a predetermined pixel size; and enhance the target image to improve the contrast using false color enhancement from values provided in a false color look-up table, and
an interface to communicate with an external device.

32. The system of claim 31, comprising:
an illumination source to illuminate the target area of the imaging member with light having the predetermined wavelength.

33. The system of claim 32, wherein the illumination source is interchangeable with another illumination source to emit energy at approximately another predetermined wavelength suitable to initiate crosslinking of the imaging sensitive layer.

34. The system of claim 31, comprising:
at least one target optic component interposed between the imaging member and the target sensor to process the second portion of the reflected light before the target sensor receives the second portion of the reflected light.

35. The system of claim 32, comprising:
a first filter interposed between the imaging member and the illumination source to polarize the light emitted from the illumination source.

36. The system of claim 32, wherein the first filter is formed integrally with the illumination source.

37. The system of claim 36, wherein the illumination source is a polarizing light-emitting diode.

38. The system of claim 35, comprising:
a second filter interposed between the imaging member and the target sensor to polarize the light reflected from the imaging member.

39. The system of claim 31, comprising:
a beam splitter interposed between the imaging member and the target sensor to split the light reflected from the imaging member in two separate paths.

40. The system of claim 31, comprising:
a display coupled to the processor to display either the target image or the measure image in response to an external input.

41. The system of claim 32, wherein the illumination source comprises:
one or more light sources to emit light at the predetermined wavelength.

42. The system of claim 41, wherein the one or more light sources emit light at any of a visible and invisible spectrum.

43. The system of claim 31, wherein the target area portion of the imaging member comprises any one of a latent and non-latent image.

44. The system of claim 31, wherein the interface is any one of a wired interface and a wireless interface.

45. The system of claim 31, comprising:
a platesetter coupled to said interface.

46. The system of claim 31, comprising:
a computer coupled to said interface.

* * * * *